(12) United States Patent
Hagino et al.

(10) Patent No.: US 7,806,266 B2
(45) Date of Patent: Oct. 5, 2010

(54) MICROPORE FORMING SYSTEM, MICROPORE FORMING DEVICE, CHIP CONTAINER, AND CHIP CONTAINER KIT

(75) Inventors: Kei Hagino, Kobe (JP); Yasunori Maekawa, Kobe (JP); Kenichi Sawa, Nishinomiya (JP); Katsutoshi Mishima, Sanda (JP); Mitsuhiro Tatsuzumi, Hyogo (JP)

(73) Assignee: Sysmex Corporation, Kobe (JP)

( * ) Notice: Subject to any disclaimer, the term of this patent is extended or adjusted under 35 U.S.C. 154(b) by 212 days.

(21) Appl. No.: 11/717,308

(22) Filed: Mar. 13, 2007

(65) Prior Publication Data
US 2007/0233011 A1 Oct. 4, 2007

(30) Foreign Application Priority Data
Mar. 13, 2006 (JP) .............................. 2006-067098

(51) Int. Cl.
*A61B 17/06* (2006.01)
*B65D 83/10* (2006.01)

(52) U.S. Cl. .................... 206/438; 206/363; 206/359

(58) Field of Classification Search .................. 604/19, 604/22, 46, 47, 173, 403; 606/186; 206/63.3, 206/440, 438, 370, 367, 359, 366, 587; 220/503, 220/504
See application file for complete search history.

(56) References Cited

U.S. PATENT DOCUMENTS

| | | | | |
|---|---|---|---|---|
| 3,061,136 A | * | 10/1962 | Sterngart | 220/504 |
| 3,444,989 A | * | 5/1969 | Hertel et al. | 206/229 |
| 3,675,766 A | * | 7/1972 | Rosenthal | 206/367 |
| 3,833,146 A | * | 9/1974 | Braginetz | 221/66 |
| 4,106,620 A | * | 8/1978 | Brimmer et al. | 206/363 |
| 4,222,392 A | * | 9/1980 | Brennan | 600/556 |
| 5,222,599 A | * | 6/1993 | Boyce | 206/366 |
| 5,402,885 A | * | 4/1995 | Cook et al. | 206/723 |
| 5,487,726 A | * | 1/1996 | Rabenau et al. | 604/46 |
| 6,036,924 A | | 3/2000 | Simons et al. | |
| 2002/0091357 A1 | | 7/2002 | Trautman et al. | |
| 2002/0169411 A1 | | 11/2002 | Sherman et al. | |
| 2007/0083151 A1 | * | 4/2007 | Carter | 604/46 |

FOREIGN PATENT DOCUMENTS

WO WO 02/30301 A1 4/2002

OTHER PUBLICATIONS

Partial European Search Report for Application No. 07005037 dated Aug. 8, 2007.
European Office Action issued Dec. 2, 2008 in European application No. 07 005 037.2, 6 pages.

* cited by examiner

*Primary Examiner*—J. Gregory Pickett
*Assistant Examiner*—Kaushikkumar Desai
(74) *Attorney, Agent, or Firm*—Brinks Hofer Gilson & Lione

(57) ABSTRACT

A micropore forming system comprising: a microneedle chip having microneedles for forming micropores in a skin of a living body; a chip container for detachably housing the microneedle chip; and a micropore forming device for detachably holding the microneedle chip and for contacting the microneedles of the microneedle chip to the skin.

7 Claims, 19 Drawing Sheets

[Fig. 1]
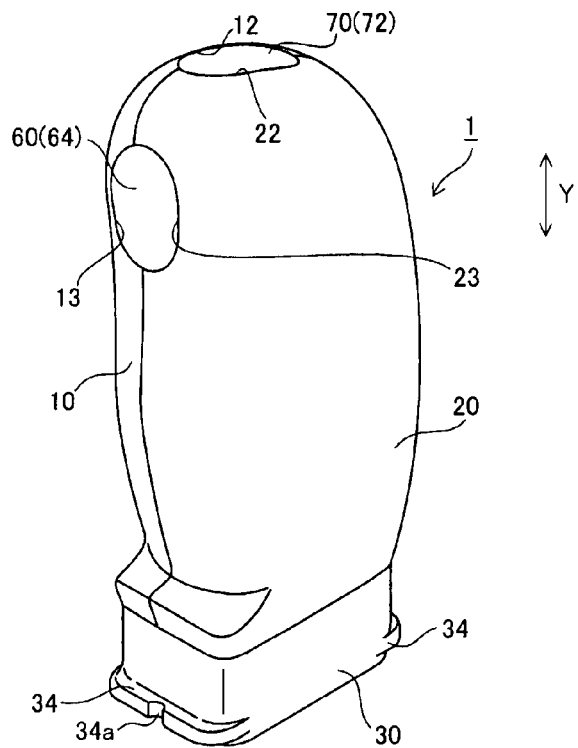
[Fig. 2]
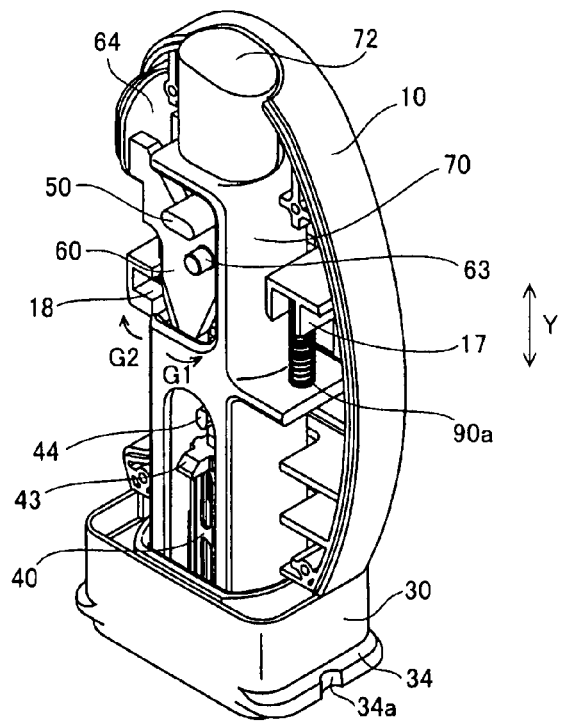

[Fig. 3]
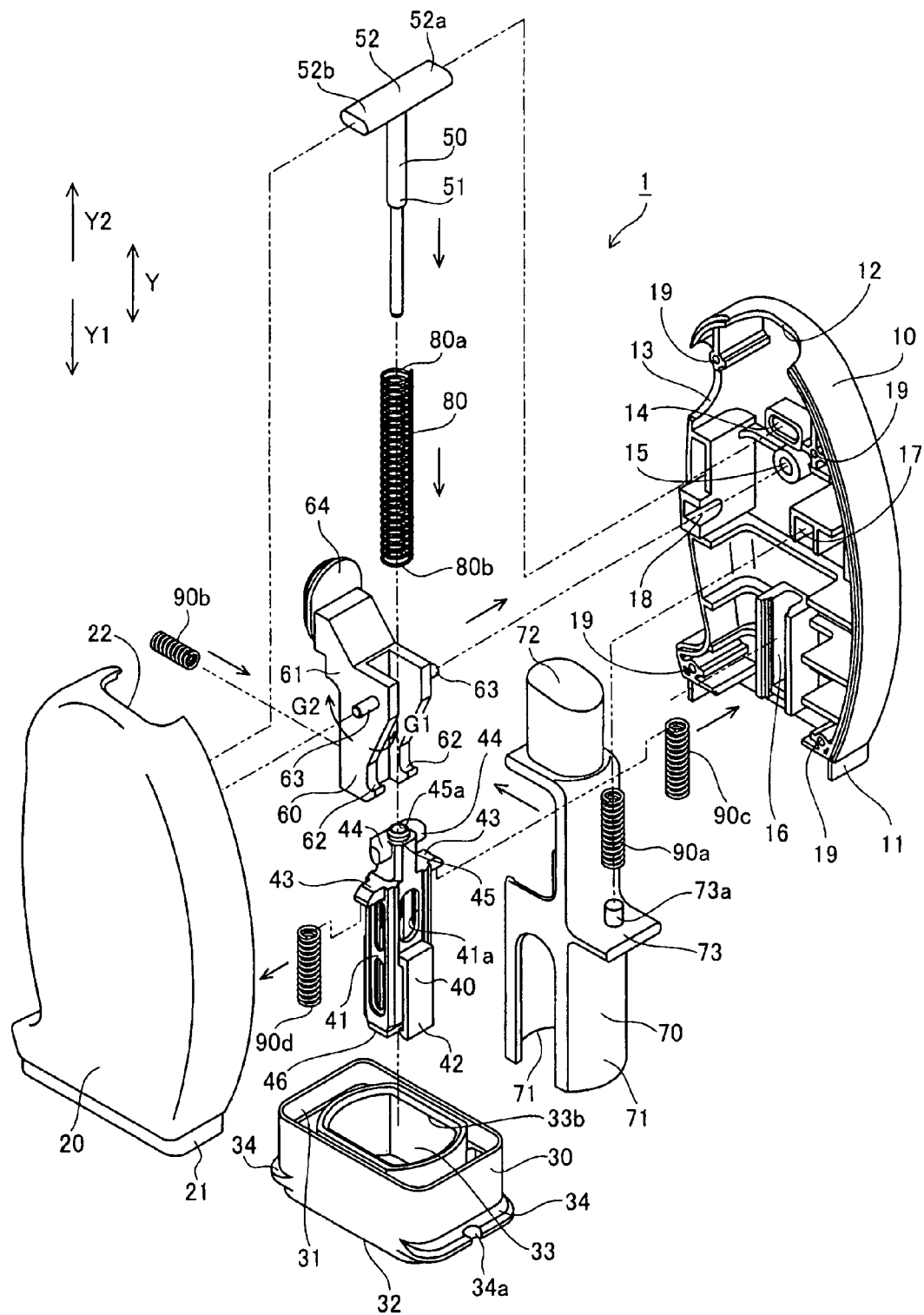

[Fig. 4]
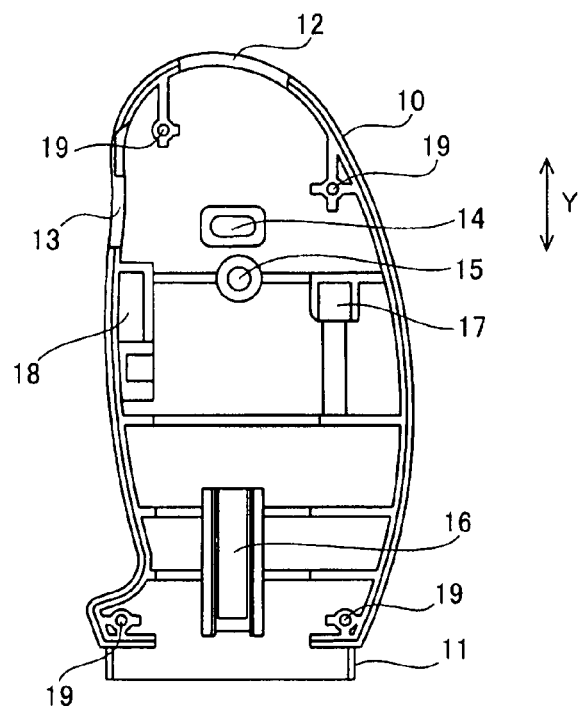
[Fig. 5]
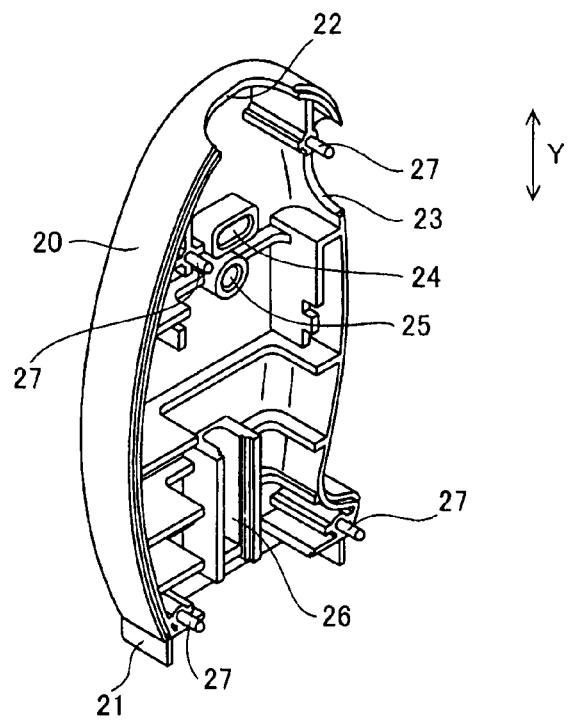

[Fig. 6]
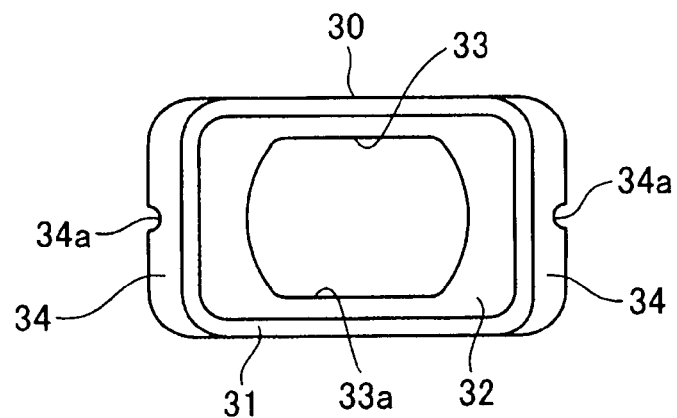
[Fig. 7]
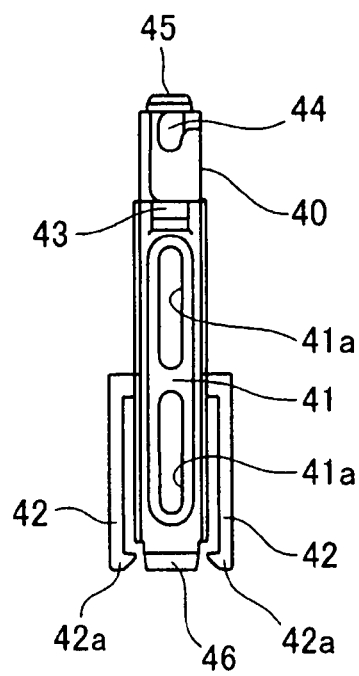

[Fig. 8]
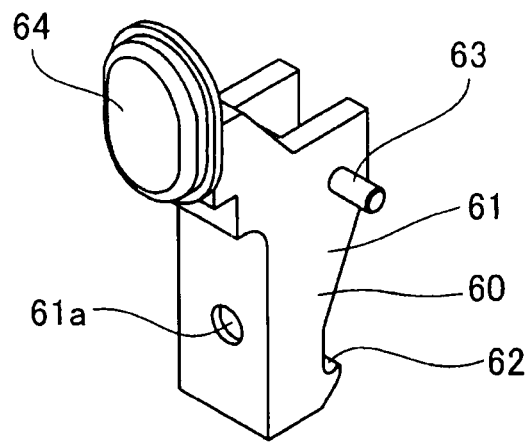
[Fig. 9]
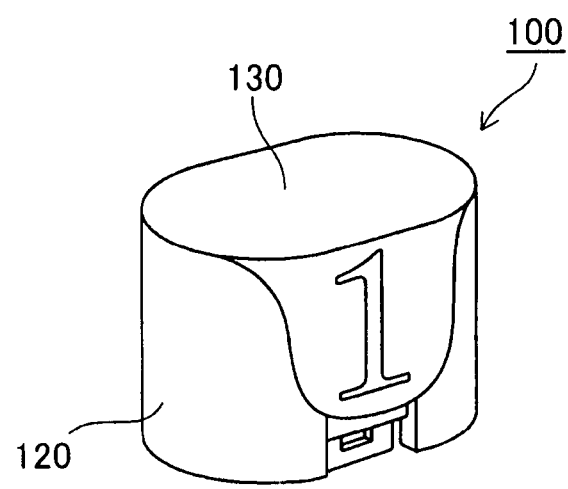

[Fig. 10]
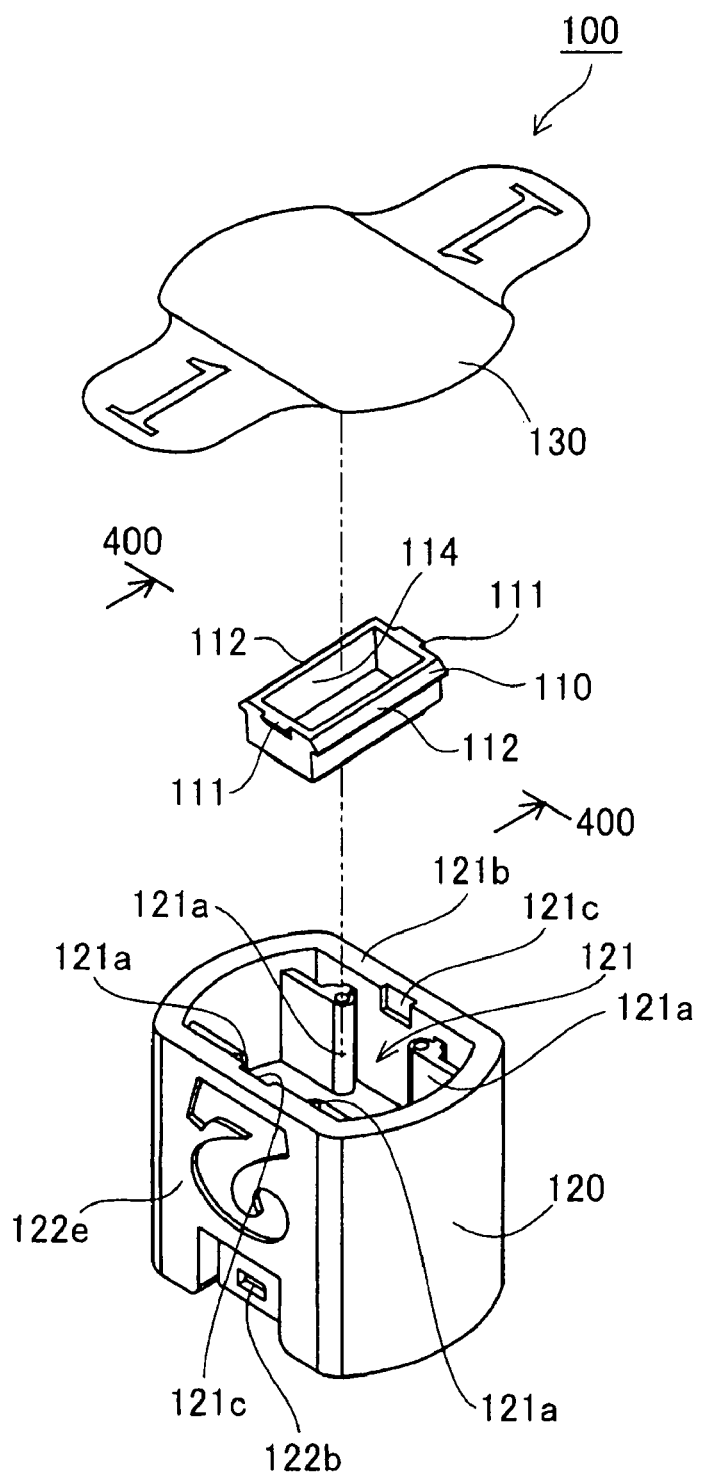

[Fig. 11]
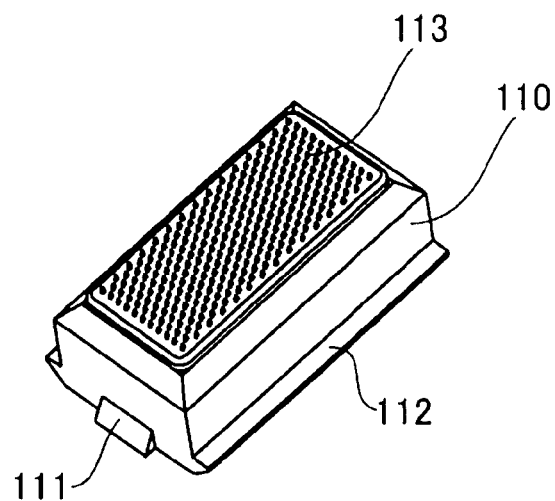
[Fig. 12]
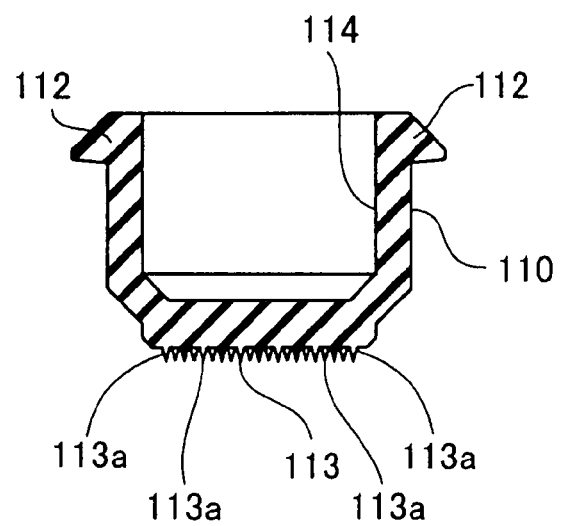

[Fig. 13]
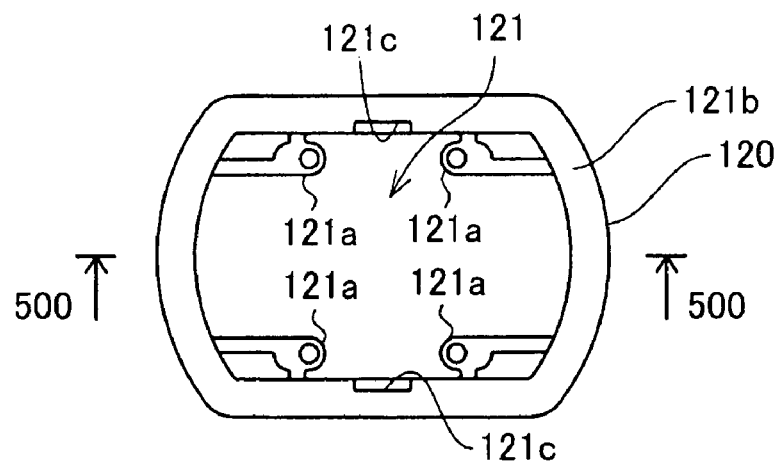
[Fig. 14]
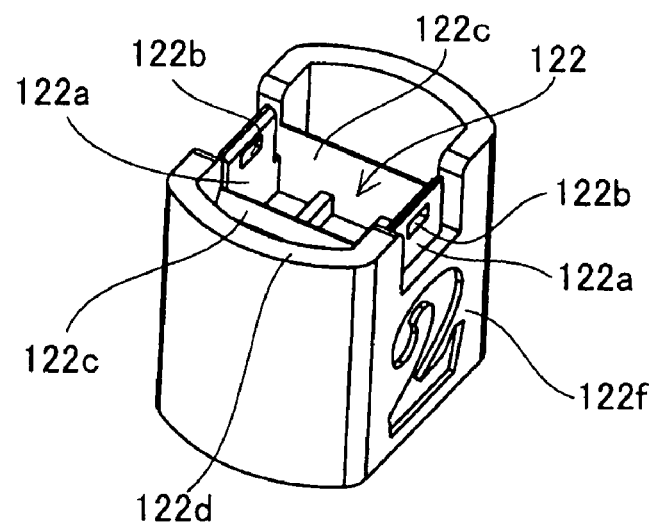

[Fig. 15]
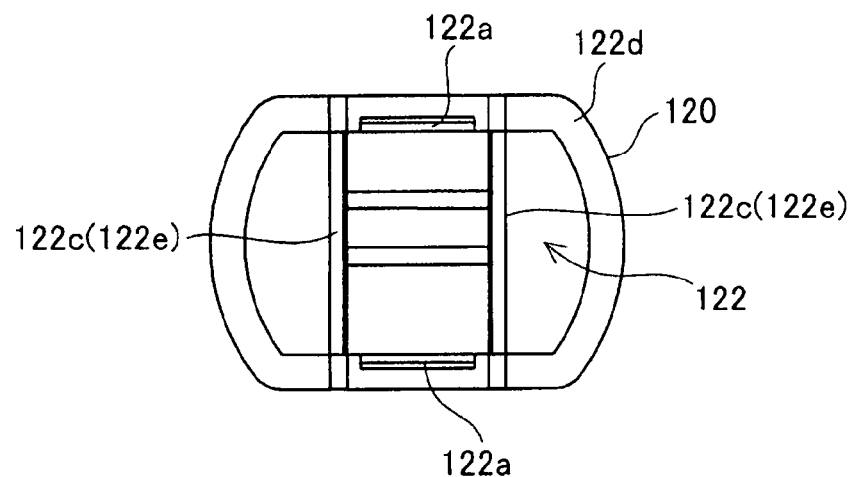
[Fig. 16]
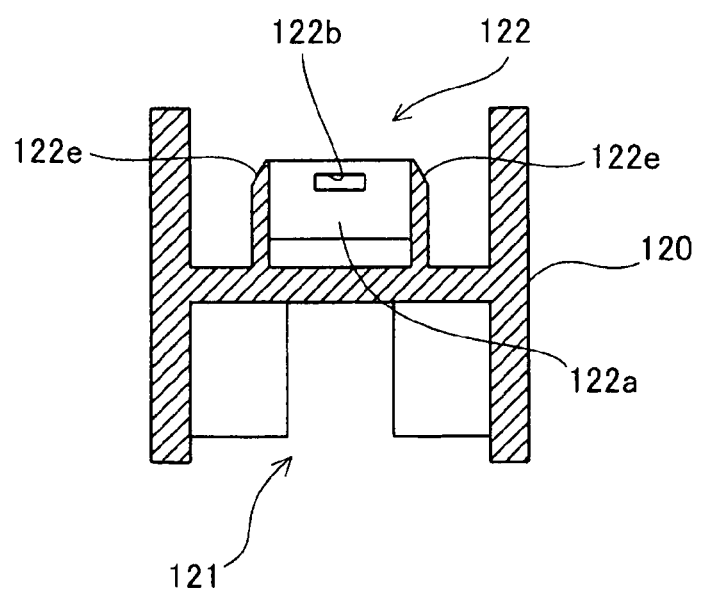

[Fig. 17]
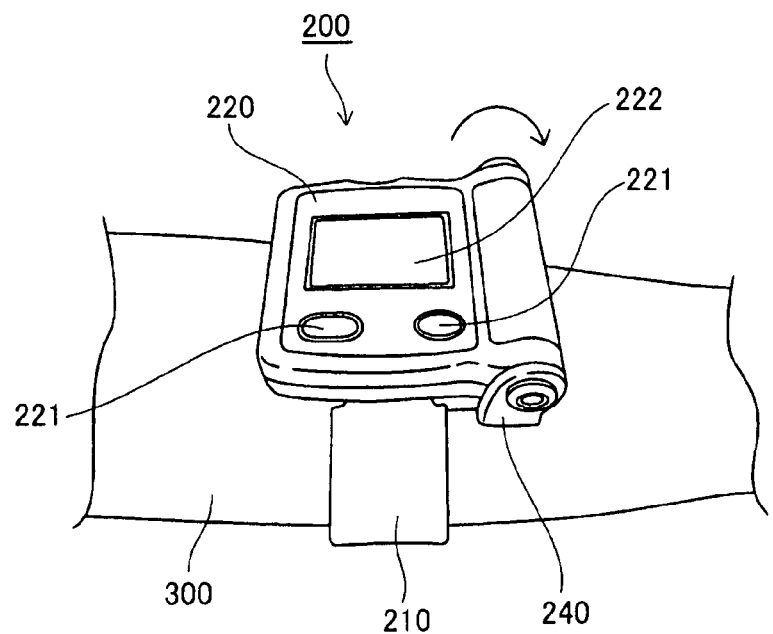
[Fig. 18]
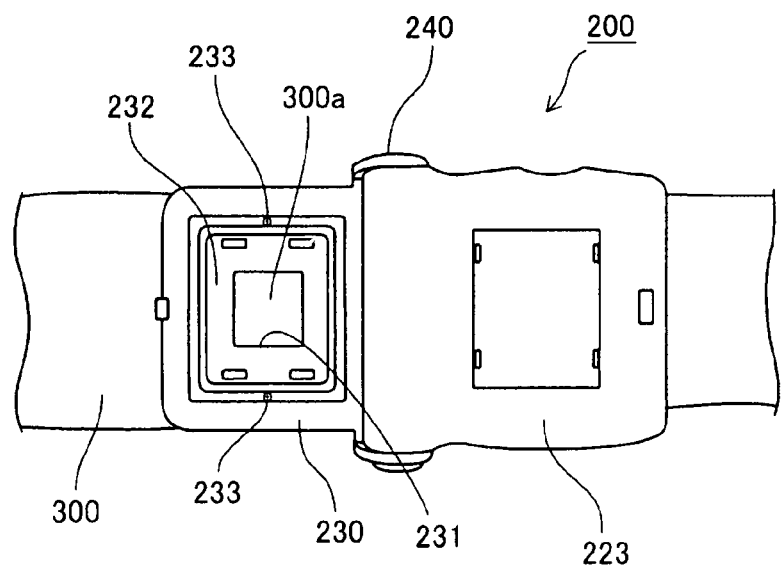

[Fig. 19]
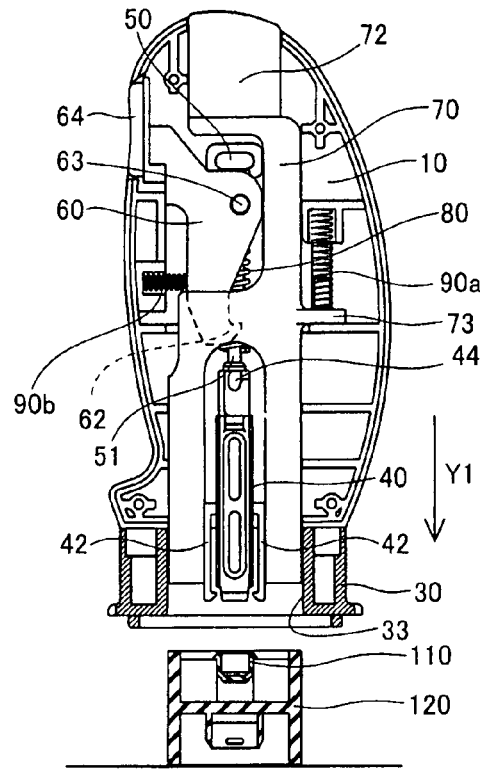
[Fig. 20]
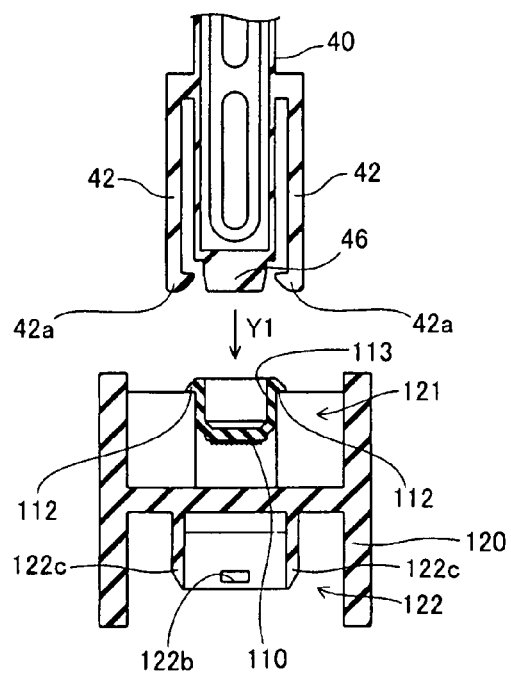

[Fig. 21]
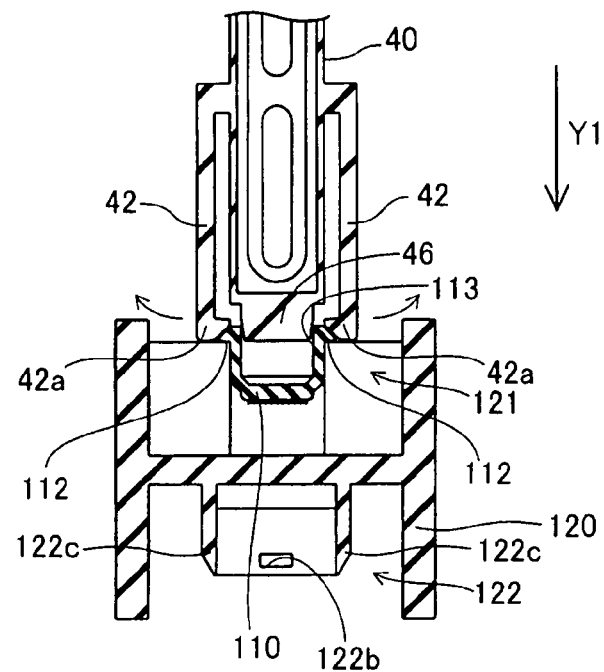
[Fig. 22]
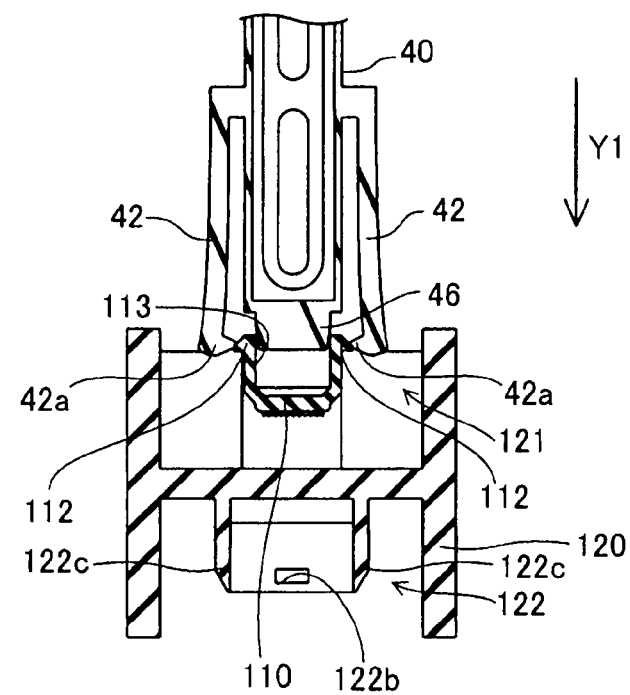

[Fig. 23]
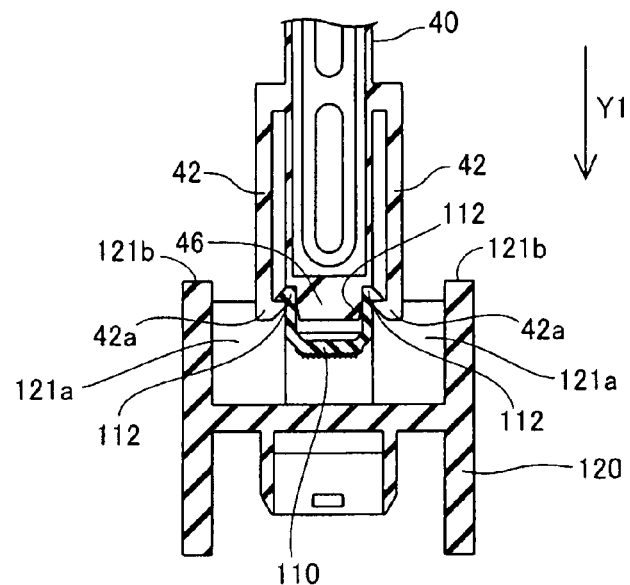
[Fig. 24]
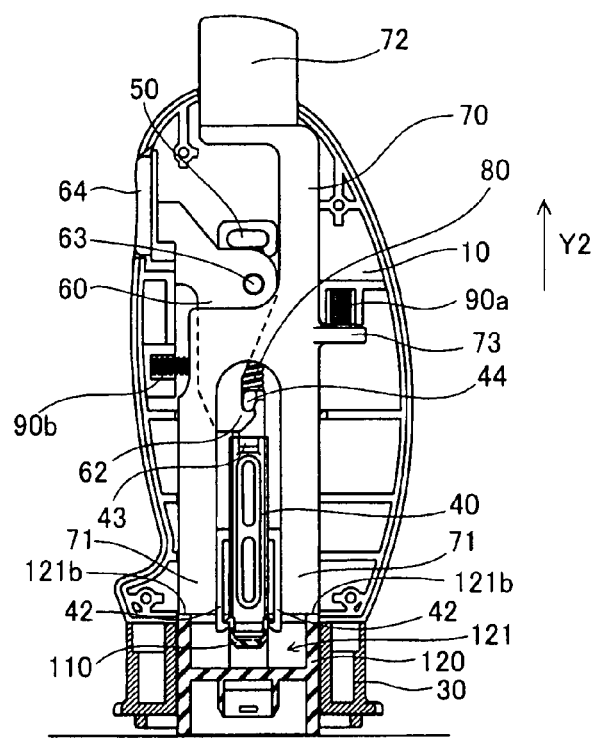

[Fig. 25]
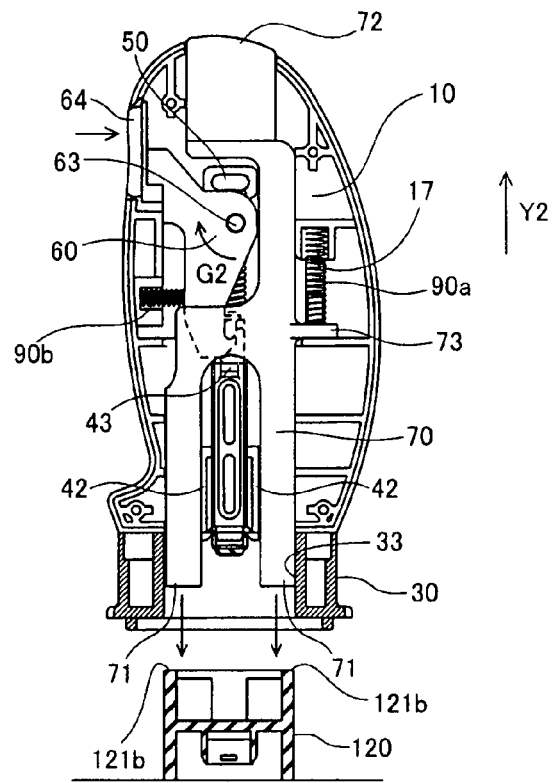
[Fig. 26]
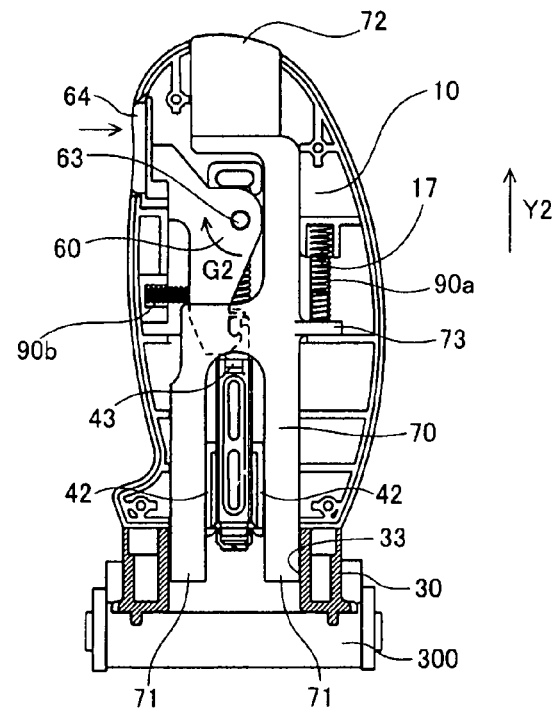

[Fig. 27]
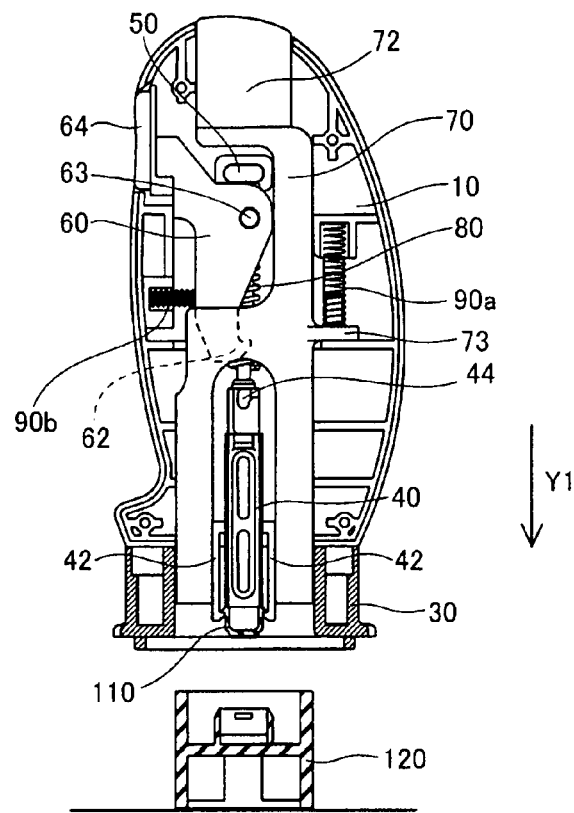
[Fig. 28]
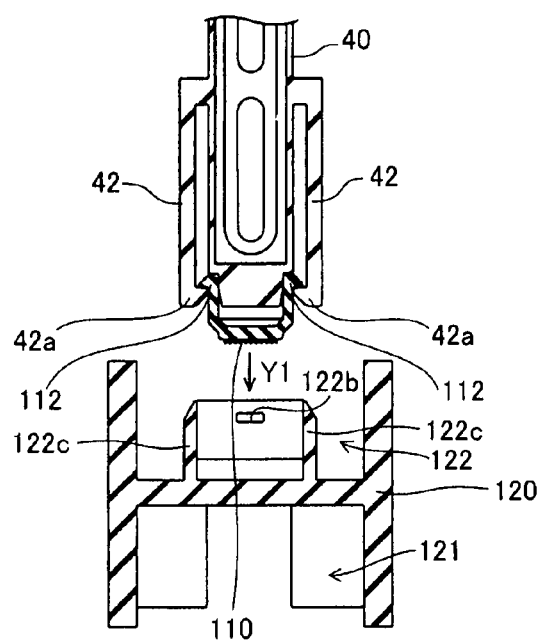

[Fig. 29]
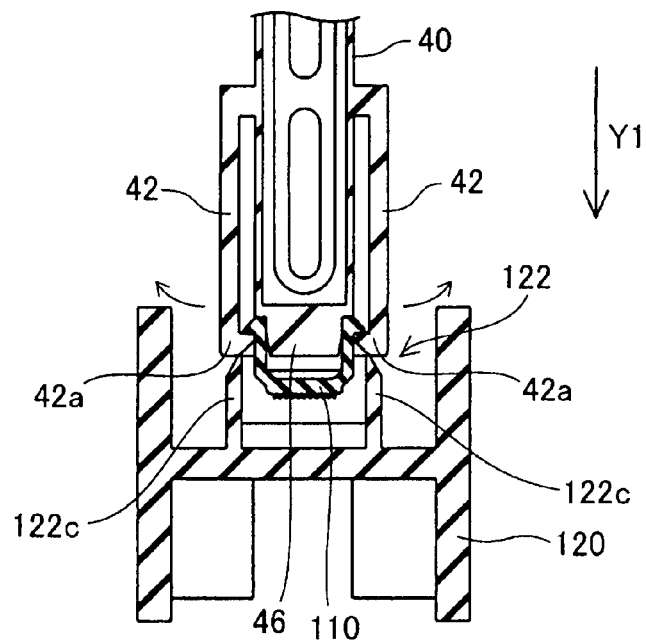
[Fig. 30]
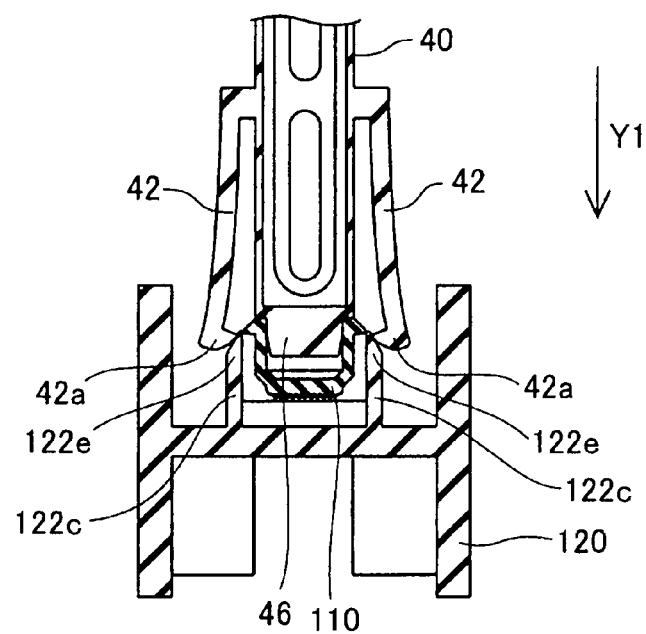

[Fig. 31]
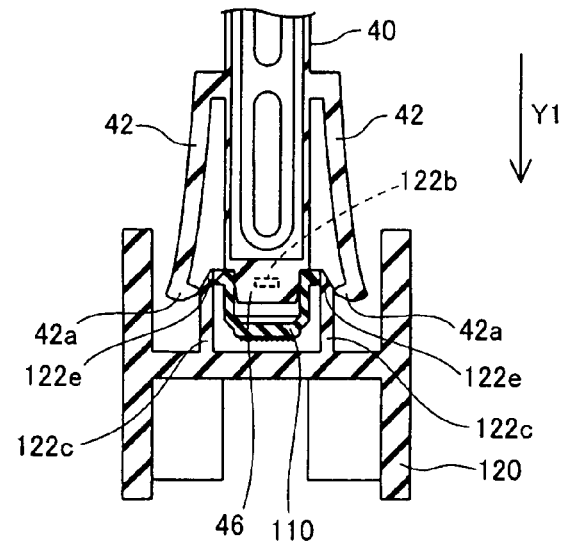
[Fig. 32]
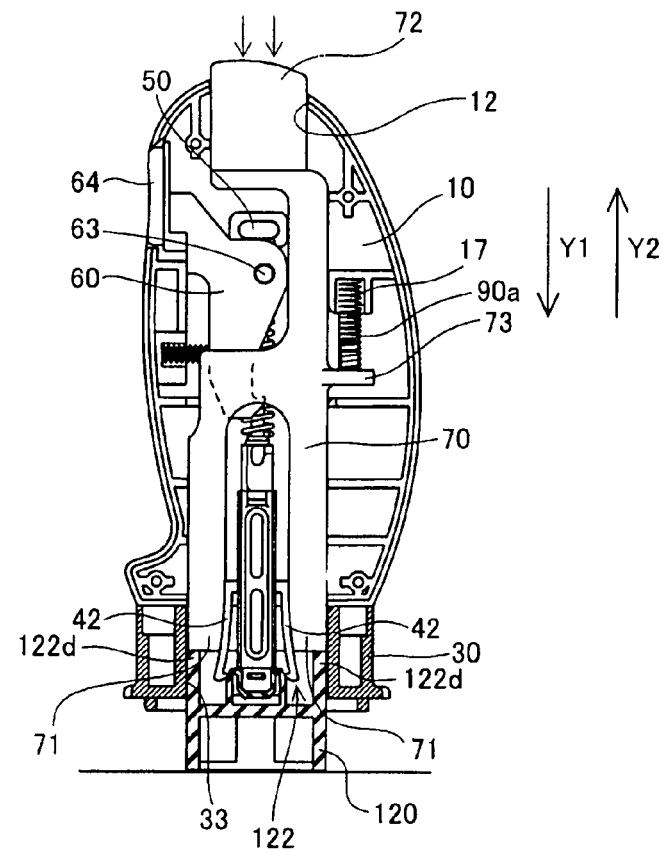

[Fig. 33]
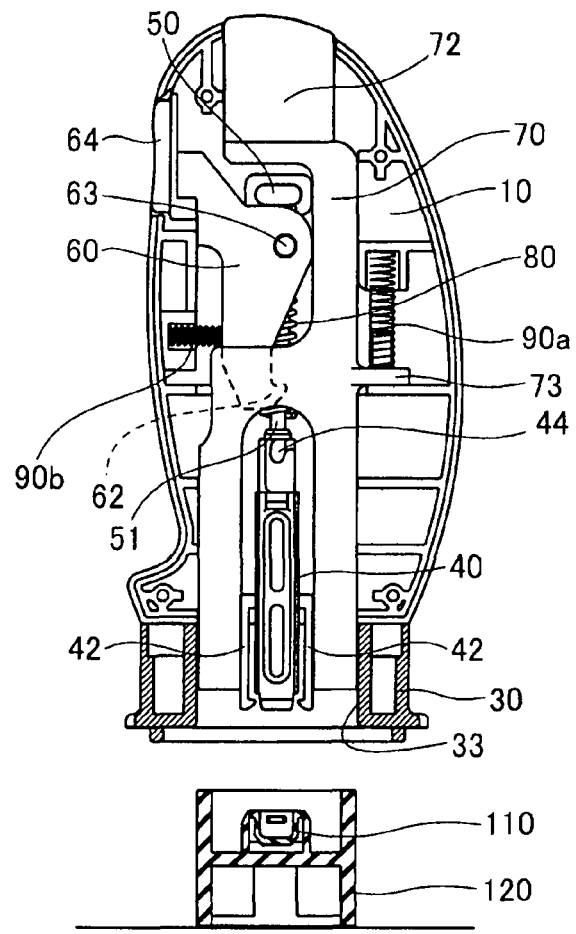
[Fig. 34]
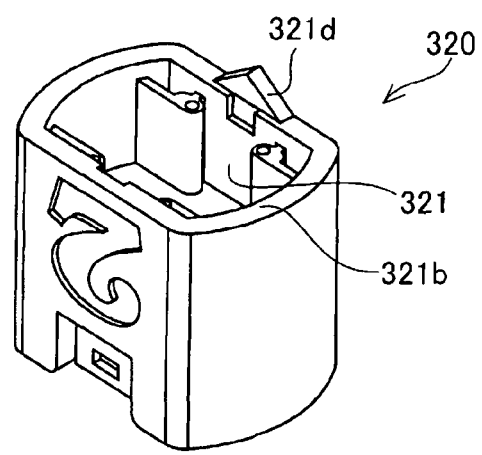

[Fig. 35]
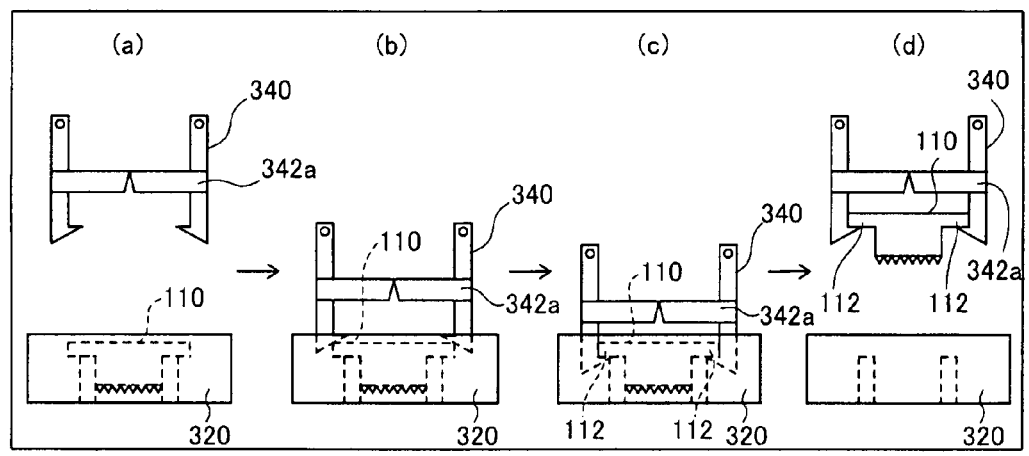
[Fig. 36]
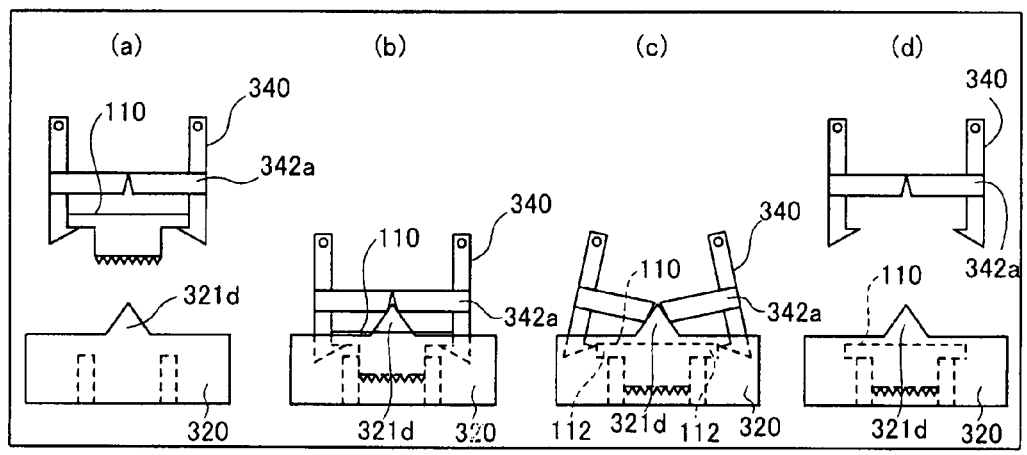

MICROPORE FORMING SYSTEM, MICROPORE FORMING DEVICE, CHIP CONTAINER, AND CHIP CONTAINER KIT

This application claims priority under 35 U.S.C. §119 to Japanese Patent Application No. JP2006-67098 filed Mar. 13, 2006, the entire content of which is hereby incorporated by reference.

FIELD OF THE INVENTION

The present invention relates to a micropore forming system, micropore forming device, chip container, and chip container kit, and specifically relates to a micropore forming system and micropore forming device using a microneedle chip for forming micropores in the skin of a living body, a chip container for housing a microneedle chip used by the micropore forming device, and a chip container kit provided with this microneedle chip.

BACKGROUND OF THE INVENTION

Known conventional microscopic pore forming devices include a piston that imparts an impact on microprotrusion member (microneedle chip), an anchoring mechanism for anchoring the piston in a state in which a spring is exerting a force, and a holding ring for holding the microprotrusion member (for example, WO/2002/030301).

When the microscopic pore forming device disclosed in WO/2002/030301 is used, the piston is anchored by the anchoring mechanism in a state in which a force is exerted by the spring, a holding ring is installed at the bottom part of the piston, the holding ring is positioned adjacent to the skin, the piston applies an impact on the microprotrusion member by removing the anchoring mechanism, and microscopic pores are formed via the impact of the microprotrusion member on the skin.

In the microscopic pore forming device disclosed in WO/2002/030301, however, since the microprotrusion member must be removed from the holding ring in order to again form microscopic pores, a new microprotrusion member must be held on the holding ring manually by the operator and that may lead to contamination of the microprotrusion member.

SUMMARY OF THE INVENTION

The scope of the present invention is defined solely by the appended claims, and is not affected to any degree by the statements within this summary.

A first aspect of the present invention is a micropore forming system comprising: a microneedle chip having microneedles for forming micropores in a skin of a living body; a chip container for detachably housing the microneedle chip; and a micropore forming device for detachably holding the microneedle chip and for contacting the microneedles of the microneedle chip to the skin.

A second aspect of the present invention is a micropore forming method for forming micropores in a skin of a living body comprising: providing a micropore forming device and a chip container housing a microneedle chip; installing the microneedle chip in the micropore forming device from the chip container; and forming micropores in the skin by contacting the microneedles of the microneedle chip to the skin using the micropore forming device.

A third aspect of the present invention is a micropore forming device comprising: a holder for detachably holding a microneedle chip having microneedles for forming micropores in a skin of a living body by contacting the skin; wherein the holder holds the microneedle chip by contacting the microneedles of the microneedle chip housed in the chip container.

A fourth aspect of the present invention is a chip container comprising: a first holder for detachably holding a microneedle chip which is installed in a micropore forming device for forming micropores in a skin of a living body; and a second holder for holding a microneedle chip that has been removed from the micropore forming device.

A fifth aspect of the present invention is a chip container comprising: a chip holder for detachably holding a microneedle chip which is installed in a micropore forming device for forming micropores in a skin of a living body; wherein the chip holder is capable of holding a microneedle chip that has been removed from the micropore forming device.

A sixth aspect of the present invention is a chip container kit comprising: a microneedle chip which has microneedles and is installed in a micropore forming device for forming micropores in a skin of a living body; a chip container comprising a first holder which detachably holds a microneedle chip, and a second holder for holding a microneedle chip that has been removed from the micropore forming device; and a seal member for covering an opening of the first holder and for maintaining the microneedle chip held by the first holder under a sterilized condition.

BRIEF DESCRIPTION OF THE DRAWINGS

FIG. 1 is a perspective view showing the overall structure of a piercing tool of an embodiment of the present invention;

FIG. 2 is a perspective view showing the internal structure of the piercing device of the embodiment shown in FIG. 1;

FIG. 3 is an exploded perspective view of the piercing device of the embodiment shown in FIG. 1;

FIG. 4 is a front elevation view of the internal structure of the rear cover of the piercing device of the embodiment shown in FIG. 1;

FIG. 5 is a perspective view of the internal structure of the front cover of the piercing device of the embodiment shown in FIG. 1;

FIG. 6 is a bottom view of the chip container insertion member of the piercing device of the embodiment shown in FIG. 1;

FIG. 7 is a front elevation view array chuck of the piercing device of the embodiment shown in FIG. 1;

FIG. 8 is a perspective view of the release button of the piercing device of the embodiment shown in FIG. 1;

FIG. 9 is a perspective view showing the overall structure of the chip container kit provided with a microneedle chip installed in the piercing device of the embodiment shown in FIG. 1;

FIG. 10 is an exploded perspective view of the chip container kit shown in FIG. 9;

FIG. 11 is a perspective view of the microneedle chip of the chip container kit shown in FIG. 9;

FIG. 12 is a cross section view of the microneedle chip along ling 400-400 in FIG. 10;

FIG. 13 is a top view of the chip container of the chip container kit shown in FIG. 9;

FIG. 14 is a perspective view of the chip container of the chip container kit shown in FIG. 9;

FIG. 15 is a bottom view of the chip container of the chip container kit shown in FIG. 9;

FIG. 16 is a cross section view of the chip container along the line 500-500 in FIG. 13;

FIG. 17 is a top view showing a blood sugar analyzer, which uses the piercing device of the first embodiment shown in FIG. 1, mounted on the arm of a user;

FIG. 18 is a perspective view showing the rotated main body of the blood sugar analyzer of FIG. 17;

FIG. 19 illustrates the use sequence of the piercing device of the embodiment shown in FIG. 1;

FIG. 20 illustrates the use sequence of the piercing device of the embodiment shown in FIG. 1;

FIG. 21 illustrates the use sequence of the piercing device of the embodiment shown in FIG. 1;

FIG. 22 illustrates the use sequence of the piercing device of the embodiment shown in FIG. 1;

FIG. 23 illustrates the use sequence of the piercing device of the embodiment shown in FIG. 1;

FIG. 24 illustrates the use sequence of the piercing device of the embodiment shown in FIG. 1;

FIG. 25 illustrates the use sequence of the piercing device of the embodiment shown in FIG. 1;

FIG. 26 illustrates the use sequence of the piercing device of the embodiment shown in FIG. 1;

FIG. 27 illustrates the use sequence of the piercing device of the embodiment shown in FIG. 1;

FIG. 28 illustrates the use sequence of the piercing device of the embodiment shown in FIG. 1;

FIG. 29 illustrates the use sequence of the piercing device of the embodiment shown in FIG. 1;

FIG. 30 illustrates the use sequence of the piercing device of the embodiment shown in FIG. 1

FIG. 31 illustrates the use sequence of the piercing device of the embodiment shown in FIG. 1;

FIG. 32 illustrates the use sequence of the piercing device of the embodiment shown in FIG. 1;

FIG. 33 illustrates the use sequence of the piercing device of the embodiment shown in FIG. 1

FIG. 34 is a perspective view showing a modification of the chip container shown in FIG. 10;

FIG. 35 illustrates the sequence for mounting the unused microneedle chip, which is housed in the ship housing device shown in FIG. 10, on the array chuck; and FIG. 36 illustrates the sequence for removing the used microneedle chip, which is in the chip container shown in FIG. 10, from the array chuck.

DETAILED DESCRIPTION OF THE PREFERRED EMBODIMENTS

A embodiment of the present invention is described hereinafter based on the drawings.

A piercing device 1 of an embodiment of the present invention (refer to FIG. 1) has an installed microneedle chip 110 that has been treated with a sterilization process (refer to FIG. 11), and forms fluid extraction holes (micropores) in the skin of a living body by having the microneedle 113a of the microneedle chip 110 abut the skin of a living body (for example, the skin of a human body). Then, a diabetic patient can self-monitor and manage his blood sugar level by calculating his blood sugar value through analyzing fluid (interstitial fluid) extracted from the extraction holes in the skin of the living body that have been formed by the piercing device 1 and microneedle chip 110 using a blood sugar analyzer 200 (refer to FIGS. 17 and 18), which calculates the blood sugar level. First, the structure of the piercing device 1 of the embodiment of the present invention is described in detail with reference to FIGS. 1 through 8, 11, 12, 17 and 18.

The piercing device 1 forms a plurality of small extraction holes through the skin which attain the corium but do not reach the subcutaneous tissue, and extracts interstitial fluid from these extraction holes. As shown in FIGS. 1 through 3, the piercing device 1 is provided with rear cover 10, front cover 20, chip container insertion member 30, array chuck 40, spring stopper 50, release button 60, ejector 70, main spring 80 (refer to FIG. 3), and a plurality of springs 90a through 90d (refer to FIG. 3). Excluding the springs (main spring 80 and plurality of springs 90a through 90d), the seven members (rear cover 10, front cover 20, chip container insertion member 30, array chuck 40, spring stopper 50, release button 60, ejector 70) are respectively formed of resin.

A case configured by the rear cover 10 and front cover 20 contains the chip container insertion member 30, array chuck 40, spring stopper 50, release button 60, ejector 70, main spring 80, and a plurality of springs 90a through 90d, as shown in FIGS. 2 and 3. The bottom of the rear cover 10 is provided with a mounting part 11 for mounting the chip container insertion member 30, as shown in FIGS. 3 and 4. At the top of the rear cover 10 is provided an opening 12 which exposes a button part 72 of the ejector 70 that the user can push. At the side of the rear cover 10 is provided an opening 13 for exposing a button part 64 of the release button 60. Inside the rear cover 10 are provided a concavity 14 for accepting one end 52a of a spring contact part 52 of the spring stopper 50, a concavity 15 for engaging a support shaft 63 of the release button 60, a guide channel 16 for guiding a guide part 43 of the array chuck 40 that moves in the Y direction within the casing, spring installation parts 17 and 18 for respectively installing the springs 90a and 90b, and four boss insertion holes 19 for inserting four bosses of the front cover 20 (refer to FIG. 5). The spring 90c is installed in the guide channel 16.

As shown in FIGS. 3 and 5, the front cover 20 has, similar to the rear cover 10, a mounting part 21 for mounting the chip container insertion member 30, an opening 22 which exposes a button part 72 of the ejector 70 that the user can push, an opening 23 for exposing a button part 64 of the release button 60, a concavity 24 for accepting the other end 52b of a spring contact part 52 of the spring stopper 50, a concavity 25 for engaging a support shaft 63 of the release button 60, and a guide channel 26 for guiding a guide part 43 of the array chuck 40 that moves in the Y direction within the casing. The spring 90d (refer to FIG. 3) is installed in the guide channel 16 (refer to FIG. 5). Four bosses 27 are formed on the front cover 20 at positions opposite the four boss insertion holes 19 of the rear cover 10 (refer to FIG. 3). Thus, the front cover 20 is mounted at a fixed position relative to the rear cover 10 by inserting the four bosses 27 of the front cover 20 into the four boss insertion holes 19 of the rear cover 10.

The chip container insertion member 30 is provided to insert the chip container 120 that accommodates the microneedle chip 110 when installing the microneedle chip 110 (refer to FIG. 11), and to insert the empty chip container 120 when disposing of the used microneedle chip 110. As shown in FIGS. 3 and 5, the chip container insertion member 30 includes a mounting part 31 attached to the mounting part 21 of the front cover 20 and to the mounting part 11 of the rear cover 10, a contact surface 32 that abuts the skin side (a contact surface 232 of a receiving part 230 of the blood sugar analyzer 200 (refer to FIG. 18) of the arm 300 of a user (patient), a through hole 33 having an opening 33a formed on the contact surface 32 and an opening 33b formed on the opposite side (refer to FIG. 3), and two flanges 34 formed so as to overhang from the exterior surface toward the exterior side in the foreground direction.

In the present embodiment, the opening 33a formed on the contact surface 32 allows the insertion of the chip container 120 that accommodates the removable microneedle chip 110 (refer to FIG. 10). The chip container 120 that has passed through the opening 33a can move in the Y direction through the through hole 33 (opening 33b).

Notches 34a are provided on the two flanges 34 at locations corresponding to two pins 233 provided on the receiving part 230 (refer to FIG. 18) of the blood sugar analyzer 200.

The array chuck 40 is configured so as to be movable in the Y direction along the guide channel 16 of the rear cover 10 and the guide channel 26 of the front cover 20, and permits the microneedle chip 110 held in the array chuck 40 (refer to FIG. 11) to move in the Y direction through the through hole 33 of the chip container insertion member 30. As shown in FIGS. 3 and 7, the array chuck 40 includes a body 41 provided with a plurality of holes 41a to reduce weight, a pair of chucks 42 that are elastically deformable to hold the microneedle chip 110 by engaging a flange 112 of the microneedle chip 110 (refer to FIG. 12), two guides 43 that are inserted into the guide channel 16 of the rear cover 10 and the guide channel 26 of the front cover 20, two connecting parts 44 that engage two anchor parts 62 of the release button 60 and which are described later, convexity 45 that has a through hole 45a (refer to FIG. 3) through which the shaft 51 of the spring stopper 50 (which is described later) can be inserted, and a bushing 46 formed on the bottom side of the body 41 (the side in the arrow Y1 direction). A lead end 42a, which abuts the flange 112 of the microneedle chip 110 of the chuck 42, is formed with a tapered shape, and has a hook shape to engage the flange 112. The guide 43 is configured so as to contact one end of the spring 90c and spring 90d disposed in the guide channel 16 of the rear cover 10 and the guide channel 26 of the front cover 20.

In the present embodiment, when the two connectors 44 are not engaged with the two anchor parts 62 of the release button 60 described later, the array chuck 40 automatically holds the microneedle chip 110 housing inside the chip container 120 by inserting the chip container 120 (refer to FIG. 10) into the opening 33a of the chip container insertion member 30. Then, after the array chuck 40, which is movable in the Y direction, holds the microneedle chip 110, the connector 44 is moved in the arrow Y2 direction until it is attached to the anchor part 62.

In the present embodiment, when the two connectors 44 are not engaged with the two anchor parts 62 of the release button 60 described layer, the microneedle chip 110 held in the array chuck 40 is automatically released from the chuck 42 of the array chuck 40 by inserting the chip container 120 into the opening 33a of the chip container insertion member 30.

In the present embodiment, the chuck 42 is integratedly formed of resin together with other parts (body 41, guide 43, connector 44, convexity 45, and bushing 46).

The spring stopper 50 is provided to support the main spring 80 that exerts a force on the array chuck 40 in the arrow Y1 direction. As shown in FIG. 3, the spring stopper 50 includes a shaft 51 that is inserting inside the main spring 80, and a spring contact 52 for preventing the main spring 80 from coming out in an upward direction (arrow Y2 direction) once the shaft 51 is inserted. One end 52a and the other end 52b of the spring contact 52 are formed so as to fit into the concavity 15 of the rear cover 10 and the concavity 24 of the front cover 20 (refer to FIG. 5).

As shown in FIGS. 3 and 8, the release button 60 is provided with a body 61, two anchor parts 62 for engaging two connectors 44 of the array chuck 40, two support shafts 63 for engaging the concavity 15 of the rear cover 10 and the concavity 25 of the front cover 20 (refer to FIG. 5), and a button part 64 exposed from the opening 13 provided on the side surface of the rear cover 10 and the opening 23 provided on the side surface of the front cover 20 (refer to FIG. 5). On the side surface of the body 61 provided with the button part 64 is a concavity 61a for abutting one end of the spring 90b (refer to FIG. 3) installed on the spring installation part 18 of the rear cover 10 (refer to FIGS. 3 and 4), as shown in FIG. 8. In the present embodiment, the two anchor parts 62 function to anchor the array chuck 40 that moves in the arrow Y2 direction against the force exerted in the arrow Y1 direction by the main spring 80 described later.

In the present embodiment, the ejector 70 functions to eject the chip container 120, which accommodates the microneedle chip 110, from the through hole 33 of the chip container insertion member 30 (refer to FIG. 3). As shown in FIG. 3, the ejector 70 includes a pressing part 71 that presses the edge 121b and the edge 122d of the chip container 120 described later (refer to FIG. 10), a boss part 72 that is exposed through the opening 12 of the rear cover 10 and the opening 22 of the front cover 20 so as to be pressable by a user, and a contact 73 that contacts one end of the spring 90a installed on the spring installation part 17 of the rear cover 10. A boss part 73a is formed on the contact 73 and is inserted inside the spring 90a to regulate the removal of the spring 90a from the spring installation part 17 of the rear cover 10.

The main spring 80 is provided to exert a force on the array chuck 40 in the arrow Y1 direction. The shaft 51 of the spring stopper 50 is inserted inside the main spring 80, as shown in FIG. 3. In this case, one end 80a of the main spring 80 abuts the spring contact 52 of the spring stopper 50, and the other end 80b abuts the top surface of the connector 44 of the array chuck 40.

The spring 90a, which is inserted on the boss part 73a of the contact 73 of the ejector 70 and installed on the spring installation part 17 of the rear cover 10, functions to exert a force in the arrow Y1 direction on the ejector 70, which has been pushed upward in the arrow Y2 direction, as shown in FIG. 3. The spring 90b, which is disposed on the spring installation part 18 of the rear cover 10 and in the concavity 61a of the release button 60 (refer to FIG. 8), is provided to rotate in the arrow G1 direction the release button 60, which has been rotated in the arrow G2 direction, by pivoting on the support shaft 63. Furthermore, the springs 90c and 90d, which are installed in the guide channel 16 of the rear cover 10 and the guide channel 26 of the front cover 20 (refer to FIG. 5), function to push back in the arrow Y2 direction the array chuck 40, which has been moved in the arrow Y1 direction by the force exerted by the main spring 80. Thus, it is possible to regulate the movement of the array chuck 40, which has been moved in the arrow Y1 direction, downward (arrow Y1 direction) from a predetermined position, and it is further possible to restrain the microneedle 113a of the microneedle chip 110 from deep penetration in the arm 300.

The chip container kit 100, which is configured by the microneedle chip 110 installed in the array chuck 40 of the piercing device 1, chip container 120 accommodating the microneedle chip 110, and sterilization maintaining seal 130, of an embodiment of the present invention are described in detail below with reference to FIGS. 1, 3, 7 through 9, and 16.

The microneedle chip 110 is installed in the array chuck 40 (refer to FIG. 7) of the piercing device 1 (refer to FIG. 1) described above, and has a plurality of microneedles 113a that form a plurality of small extraction holes to extract interstitial fluid from the skin of a living body (for example, the skin of a human body). As shown in FIGS. 10 through 12, the microneedle chip 110 has a substantially rectangular shape from a planar view, and includes a pair of projections 111 disposed so as to protrude outwardly from the exterior side surface in the foreground and background directions, a pair of flanges 112 disposed so as to protrude outwardly from the exterior side surface in a longitudinal directions, microneedle array 113 having 305 microneedles 113a, and concavity 114 into which is inserted the bushing 46 (refer to FIG. 7) of the array chuck 40 of the piercing device 1 described above. The pair of projections 111 are configured so as to engage the locking holes 122b of the chip container 120 described later, and the pair of flanges 112 are configured so as to engage the leading end 42a of the chuck 42 of the array chuck 40 (refer to FIG. 7). The microneedle chip 110 is formed of resin and includes the 305 microneedles 113a. In addition to the microneedle chip 110 that includes the microneedle array 113 having the 305 microneedles 113a, a microneedle chip that includes a microneedle array having 189 microneedles may also be used.

In the present embodiment, the resin chip container 120 includes an opening 121 for accommodating the unused and sterile microneedle chip 110 (refer to FIG. 10), and an opening 122 for accommodating the used microneedle chip 110 after it has been used to pierce the skin of a living body (skin of a human body), as shown in FIGS. 10, and 13 through 16. The opening 121 and opening 122 are provided on mutually opposite sides, and a sterilization seal 130 which is described later is adhered to seal the opening 121 that accommodates an unused microneedle chip 110. As shown in FIGS. 10 and 13, the opening 121 includes four supports 121a for supporting the side surfaces of the sterile and unused microneedle chip 110, edge 121b that abuts the pressing part 71 of the ejector 70 (refer to FIG. 3), and recessed part 121c configured so that the projection 111 of the microneedle chip 110 held by the supports 121a (refer to FIGS. 10 and 11) do not touch the edge 121b.

In the present embodiment, the opening 122 includes a holder 122a having a locking hole 122b into which are inserted the projections 111 of the used microneedle chip 110 (refer to FIGS. 10 and 11) after it has been used to pierce the skin of a living body (skin of a human body), as shown in FIGS. 14 and 15. The opening 122 is provided with a release piece 122c for releasing the engagement of the flange 112 of the microneedle chip 110 and the chuck 42 of the array chuck 40 (refer to FIG. 7) of the piercing device 1, and an edge 122d that abuts the pressing part 71 of the ejector 70 (refer to FIG. 3). The leading end part 122e of the release piece 122c has a tapered configuration as shown in FIG. 16. A mark [2] is imprinted on the side surface 122f of the chip container 120 to allow confirmation when the opening 122 is disposed on the top side, as shown in FIG. 14.

The sterilization maintaining seal 130 is formed of aluminum, and functions to prevent viruses and bacteria from adhering to the sterile microneedle chip 110 via gamma ray exposure. The sterilization maintaining seal 130 is adhered so as to cover the opening 121 that accommodates the unused microneedle chip 110, as shown in FIGS. 9 and 10. The sterilization maintaining seal 130 is adhered so as to cover and conceal the mark [2] imprinted on the on the side surface 122f of the microneedle housing device 120. A mark [1] is printed on the part adhered to the side surface 122f of the chip container 120 so as to allow confirmation that the opening 121 is disposed on the top side, as shown in FIG. 9.

The blood sugar analyzer 200 for analyzing interstitial fluid extracted by the piercing device 1 of the embodiment of the present invention is described below with reference to FIGS. 1, 6, 17, and 18. The blood sugar analyzer 200 is mounted on the arm 300 by the user (diabetic patient) of the piercing device 1. The blood sugar analyzer 200 is configured to allow placement of an extraction cartridge (not shown in the drawing) that includes a mesh sheet for filtration of interstitial fluid extracted from the arm 300 of the user.

As shown in FIGS. 17 and 18, the blood sugar analyzer 200 includes a belt 210 that wraps around the arm 300 of the user, main body 220 provided with various operation buttons 221 and display screen 222, receiver 230 for placing the piercing device 1 (refer to FIG. 1), and hinge 240 for supporting the main body 220 so as to be rotatable relative to the receiver 230. The extraction cartridge (not shown in the drawing) can be placed on the surface 223 on the opposite side form the surface provided with the operation buttons 221 and display screen 222 of the main body 220. The receiver 230 includes an opening 231 for exposing a piercing location 300a of the arm 300 of the user, contact surface 232 that abuts the contact surface 32 (refer to FIG. 6) of the chip container insertion member 30 of the piercing device 1, and two pins 233 provided at locations corresponding to two notches 34a (refer to FIG. 6) respectively provided on two flanges 34 of the chip container insertion member 30.

FIGS. 19 through 33 illustrate the use sequence of the piercing device of the embodiment shown in FIG. 1. The use sequence of the piercing device 1 of the embodiment of the present invention is described below with reference to FIGS. 1, 3 through 5, 9 through 11, 14, and 16 through 33. Before using the piercing device 1 (refer to FIG. 1), the blood sugar analyzer 200 is mounted by wrapping the belt 210 around the arm 300 of the user, as shown in FIG. 17. The piercing location 300a of the arm 300 of the user is exposed beforehand through the opening 231 of the receiver 230 of the blood sugar analyzer 200 by rotating the main body 220 of the blood sugar analyzer 200, as shown in FIG. 18. In this case, the user places the extraction cartridge (not shown in the drawing) on the surface 223 on the side opposite of the surface provided with the various operation buttons 221 and display screen 222 of the main body 220.

First, the chip container kit 100 (refer to FIGS. 9 and 10) accommodating the microneedle chip 110 is prepared when installing the microneedle chip 110 in the piercing device 1 of the present embodiment. Then, the top and bottom of the [1] printed on the sterilization maintaining seal 130 (refer to FIG. 9) of the chip container kit 100 are confirmed and positioned, and the sterilization maintaining seal 130 is peeled from the chip container 120.

From this situation, the user (patient) grips the piercing device 1 and moves the piercing device 1 in the arrow Y1 direction so as to insert the chip container 120 through the through hole 33 of the chip container insertion member 30, as shown in FIG. 19. In this case, the user is able to perform the operation one-handed since the piercing device 1 is moved relative to the chip container 120 positioned on a table or the like. Furthermore, since the through hole 33 of the chip container insertion member 30 is the same size and shape as the insertion side of the chip container 120, the microneedle chip 110 that accommodates the chip container 120 can be positioned so as to abut the array chuck 40 disposed within the piercing device 1 by inserting the chip container 120 into the through hole 30, and the array chuck 40 can easily hold the microneedle chip 110.

When the piercing device 1 is moved in the arrow Y1 direction, the array chuck 40 disposed inside the piercing device 1 also moves in the in the arrow Y1 direction, as shown in FIG. 20. The array chuck 40 moving in the arrow Y1 direction is moved to a position at which the tapered leading end 42a abuts the flange 112 of the microneedle chip 110 accommodated in the chip container 120, as shown in FIG. 21. Thereafter, the elastically deformable pair of chucks 42 are moved in the arrow Y1 direction bent to the outside via the pressure of the pair of flanges 112 by moving the piercing device 1 (array chuck 40) in the arrow Y1 direction, as shown in FIG. 22. Subsequently, the array chuck 40 grips the microneedle chip 110 when the hook-shaped leading end 42$a$ of the chuck 42 engages the flange 112 of the microneedle chip 110, as shown in FIG. 23. At this time, the bushing 46 of the array chuck 40 is inserted in the concavity 114 of the microneedle chip 110 anchored to the chip container 120. Since the spring stopper 50 of the piercing device 1 moves in the arrow Y1 direction relative to the stopping of the array chuck 40 holding the microneedle chip 110 if the piercing device 1 is pushed further in the arrow Y1 direction from this position, the main spring 80 that abuts the spring contact 52 is compressed in conjunction with the movement of the piercing device 1 in the arrow Y1 direction.

Then, the array chuck 40, which moves relatively in the arrow Y2 direction regarding the piercing device 1 that moves in the arrow Y1 direction, reaches a position at which the two connectors 44 engage the two anchor parts 62 of the release button 60, as shown in FIG. 24. At this time, the array chuck 40 is fixed to the anchor parts 62 of the release button 60 and the main spring 80 is in a compressed state. In this condition, the release button 60 rotates in the arrow G2 direction about the support shaft 63 as the spring 90$b$ is compressed while installed in the concavity 61$a$ of the release button 60 and the spring installation part 18 of the rear cover 10 (refer to FIG. 3) when the tapered anchor 62 of the bottom end pushes the connector 44 of the array chuck 40. Thereafter, the release button 60 engages the two anchors 62 and two connectors 44 via the rotation in the arrow G1 direction by the force exerted by the compressed spring 90$b$, and the array chuck 40 is fixed in place with the main spring 80 in a compressed state.

At the same time, the ejector 70, which has moved in the arrow Y1 direction together with the movement of the piercing device 1, is stopped when the pressing part 71 abuts the edge 121$b$ of the opening 121 side of the chip container 120, as shown in FIG. 24. Therefore, the spring 90$a$ of the spring installation part 17 of the rear cover 10 is compressed in conjunction with the movement of the piercing device 1 in the arrow Y1 direction. In this case, the boss part 72 of the ejector 70 protrudes to the outside through the opening 12 of the rear cover 10 and the opening 22 of the front cover 20 in conjunction with the movement of the piercing device 1 in the arrow Y1 direction. Thereafter, the edge 121$b$ of the chip container 120, which has been inserted through the through hole 33 of the chip housing insertion member 30, is pressed by the pressing part 71 of the ejector 70 via the user moving the ejector 70 in the arrow Y2 direction, and the chip container 120 is automatically extracted from the through hole 33 of the chip container insertion member 30. This occurs because the elastic spring energy of the spring 90$a$ that has been compressed by the spring installation part 17 of the rear cover 10 reaches the contact 73 of the ejector 70, and the ejector 70 exerts a force on the chip container 120 in the arrow Y2 direction. When the elastic spring energy of the spring 90$a$ is inadequate, the chip container 120 inserted in the through hole 73 can be easily ejected by the user pushing the boss part 72 (refer to FIG. 24) that protrudes to the outside.

When the arm 300 of the patient (user) is pierced using the piercing device 1 with the installed microneedle chip 110, the two notches 34$a$ of the chip container insertion member 30 of the piercing device 1 are positionally aligned with the two pins 233 of the blood sugar analyzer 200 (refer to FIG. 18), and the piercing device 1 (refer to FIG. 1) is placed in the receiver 230 of the blood sugar analyzer 200 (refer to FIG. 18). As shown in FIG. 26, the release button 60 rotates on the support shaft 63 in the arrow G2 direction while resisting the force exerted by the spring 90$b$ by pressing the button part 64 of the release button 60. Thus, the connector 44 of the array chuck 40 is released from the anchor 62 of the release button 60, and the elastic spring energy of the main spring 80 reaches the array chuck 40. Therefore, the array chuck 40 which holds the microneedle chip 110 is moved in the arrow Y1 direction.

Since the microneedle chip 110 held by the chuck 42 of the array chuck 40 passes through the through hole 33 of the chip container insertion member 30 moving in the arrow Y1 direction, the microneedles 113$a$ of the microneedle chip 110 pierce the piercing location 300$a$ (refer to FIG. 18) on the arm 300 of the patient (user) exposed from the opening 231 of the receiver 230 of the blood sugar analyzer 200. Thus, interstitial fluid can be extracted from the piercing location 300$a$ of the patient arm 300. As shown in FIG. 17, blood sugar level measurement is performed by rotating the main body 220 on which the extraction cartridge (not shown in the drawings) is placed.

Thus, the array chuck 40 and microneedle chip 110, which are moving in the arrow Y1 direction, pierce the arm 300 of the patient and immediately move in the arrow Y2 direction so as to be housed within the through hole 33 of the chip container insertion member 30. This occurs because the springs 90$c$ (refer to FIG. 3) and 90$d$ (refer to FIG. 3) in the guide channel 16 of the rear cover 10 (refer to FIG. 4) and the guide channel 26 of the front cover 20 (refer to FIG. 5), which have been compressed by the guide part 43 when the array chuck 40 moves in the arrow Y1 direction, push back the guide part 43 of the array chuck 40 in the arrow Y2 direction.

When removing the used microneedle chip 110, the chip container 120 that accommodates the used microneedle chip 110 is prepared, as shown in FIG. 27. Then, the disposition of the top and bottom of the mark [2] imprinted on the side surface 122$f$ of the chip container 120 is confirmed (refer to FIG. 9). From this situation, the user (patient) grips the piercing device 1 and moves the piercing device 1 in the arrow Y1 direction so as to insert the chip container 120 through the through hole 33 of the chip container insertion member 30. In this case, the user is able to perform the operation one-handed without touching the used microneedle chip 110 since the piercing device 1 is moved relative to the chip container 120 positioned on a table or the like.

When the piercing device 1 is moved in the arrow Y1 direction, the array chuck 40 disposed inside the piercing device 1 also moves in the arrow Y1 direction, as shown in FIG. 28. The array chuck 40 moving in the arrow Y1 direction is moved to a position at which the tapered leading end 42$a$ abuts the release piece 122$c$ of the opening 122 of the microneedle chip 110, as shown in FIG. 29. Thereafter, the elastically deformable chuck 42 is moved in the arrow Y1 direction in a bent condition via the pressure of the leading end 122$e$ of the release piece 122$c$ by moving the array chuck 40 that holds the microneedle chip 110 in the arrow Y1 direction, as shown in FIG. 30. Thereafter, the microneedle chip 110 is detached from the piercing device 1 (array chuck 40) via the release of the engagement of the chick 42 and the flange 112 of the microneedle chip 110. If the piercing device 1 is moved in the arrow Y1 direction from this disposition, the projections 111 of the microneedle chip 110 are inserted into and held by the locking holes 122$b$ of the chip container 120 (refer to FIG. 16) because the microneedle chip 110, which is pushed by the bushing 46 of the array chuck 40, is moved in the arrow Y1 direction while bending the holder 122$a$ (refer to FIG. 14), as shown in FIG. 31.

At the same time, the ejector 70, which has moved in the arrow Y1 direction, is stopped when the pressing part 71 abuts the edge 122$d$ of the opening 122 side of the chip container 120, as shown in FIG. 32. Therefore, the spring 90a of the spring installation part 17, which is disposed on the rear cover 10 of the piercing device 1 that is moving in the arrow Y1 direction, is compressed in conjunction with the movement of the piercing device 1. In this case, the boss part 72 of the ejector 70 protrudes to the outside through the opening 12 of the rear cover 10 and the opening 22 of the front cover 20 in conjunction with the movement of the piercing device 1 in the arrow Y1 direction. Thereafter, as shown in FIG. 33, the edge 122d on the opening 122 side of the chip container 120, which has been inserted into the through hole 33 of the chip container insertion member 30, is pressed by the pressing part 71 of the ejector 70 via user moving the ejector 70 in the arrow Y2 direction, and the chip container 120 is automatically ejected from the through hole 33 of the chip container insertion member 30. This occurs because the elastic spring energy of the spring 90a that has been compressed by the spring installation part 17 of the rear cover 10 reaches the contact 73 of the ejector 70, and the ejector 70 exerts a force on the chip container 120 in the arrow Y1 direction. When the elastic spring energy of the spring 90a is inadequate, the chip container 120 inserted in the through hole 73 can be easily ejected by the user pushing the boss part 72 (refer to FIG. 24) that protrudes to the outside. Thus, the used microneedle chip 110 housed in the chip container 120 can be disposed of. This completes the use of the piercing device 1.

In the present embodiment, when the engagement of the anchor 62 of the release button 60 and the connector 44 of the array chuck 40 is released as described above, the user (diabetic patient) can hold the flange 112 of the of the microneedle chip 110 on the chuck 42 of the array chuck 40 simply by moving the piercing device 1 so as to insert the chip container 120 in the opening 33a of the chip container insertion member 30 by the provision of the array chuck 40 that holds the microneedle chip 110 and inserting the chip container 120 in the opening 33a of the chip container insertion member 30. In this case, anchoring is achieved by the anchor 62 while the array chuck 40 is moved in the arrow Y1 direction against the force exerted by the main spring 80 at the same time that the microneedle chip 110 is held by the array chuck 40 by providing the anchor 62 (release button 60) to engage the connector 44 of the array chuck 40 so as to anchor the array chuck 40 and making the array chuck 40 movable in the Y directions. Thus, the user can place the piercing device 1 when the array chuck 40, which holds the microneedle chip 110, is anchored and exerting a force toward (arrow Y2 direction) the skin of a living body (arm 300). Therefore, the user can place the piercing device 1 in a condition that allows micropores to be formed in the skin of a living body (skin of the user) without a complex operation simply by moving the piercing device 1. Then, from this condition, the microneedle chip 110 can be moved in the arrow Y2 direction through the opening 33a of the chip container insertion member 30 and micropores can be formed in the piercing location 300a of the arm 300 of the user by releasing the engagement of the anchor 62 and connector 44 of the array chuck 40 via pressing the button part 634 of the release button 60.

In the present invention, when the microneedle chip 110 is held by the array chuck 40 and the engagement is released between the anchor 62 and the connector 44 of the array chuck 40, the user can easily remove the used microneedle chip 110 held by the array chuck 40 that has been released from engagement with the anchor 62 by simply inserting the piercing device 1 as though to insert the chip container 120 in the opening 33a of the chip container insertion member 30 by inserting an empty chip container 120 that does not contain a microneedle chip 110 into the opening 33a of the chip container insertion member 30. As a result, the user can safely dispose of the used microneedle chip 110 without touching the used microneedle chip 110.

In the present embodiment, not only can the unused microneedle chip 110 used in the piercing device 1 be held by the chip container 120, the used microneedle chip 110 that has been removed from the piercing device 1 can also be detachably held by the chip container 120 by providing the opening 121 for holding the detached microneedle chip 110 and providing the opening 122 that holds the microneedle chip 110 that has been removed from the piercing device 1.

In the present invention, the used microneedle chip 110 with interstitial fluid (liquid) adhered after piercing the arm 300 can be prevented from detaching from the opening 122 by providing the locking holes 122b that prevent the detachment of the held microneedle chip 110 from the opening 122 of the chip container 120. As a result, the user can safely dispose of the chip container 120 that holds the used microneedle chip 110.

In the present embodiment, the microneedle chip 110 installed in the array chuck 40 of the piercing device 1 can be easily removed by providing a tapered release piece 122c on the part of the opening 112 abutting the leading end 42a of the chuck 42 of the array chuck 40 that holds the microneedle chip 110

The embodiment of this disclosure should be considered in all aspects an example and not in any way limiting. The scope of the present invention is defined by the scope of the claims and not by the description of the present invention, and includes all modifications within the scope of the claims and the meaning and equivalences therein.

For example, although the example of a microneedle chip having 305 or 189 microneedles is described in the present embodiment, the present invention is not limited to these numbers inasmuch as a microneedle chip having a plurality of microneedles other than 305 or 189 may also be used, and even a microneedle chip having a single microneedle may be used.

Although an example using a chip container in which a concavity for housing an unused microneedle chip and a concavity for housing a used microneedle chip are provided on mutually opposite sides, the present invention is not limited to this arrangement inasmuch as a concavity for housing an unused microneedle chip and a concavity for housing a used microneedle chip may be provided on the same side.

Although an example of configuring the chuck part that holds the microneedle chip of elastically deformable resin is described in the embodiment above, the present invention is not limited to this arrangement inasmuch as a chuck part formed of a material other than resin (for example, metal) may be used as the chuck part that holds the microneedle chip.

Although the example of the above embodiment describes moving the array chuck to compress a main spring by moving a piercing device relative to a chip container, and anchoring the array chuck to an anchor part of a release button when the main spring is in a compressed state, the present invention is not limited to this arrangement inasmuch as a lever may be provided to move the array chuck, such that a user may move the array chuck to compress a main spring by operating the lever, and the array chuck may be anchored to an anchor part of a release button when the main spring is in a compressed state.

The above embodiment has been described in terms of a chip container having two openings and providing four supports to hold the unused microneedle chip at one or another of the openings, and providing a holder that has locking holes for holding a used microneedle chip in the other opening.

However, the present invention is not limited to this arrangement inasmuch as a support may be provided to hold the unused microneedle chip and a holder may be provided to hold a used microneedle chip at a single opening. For example, supports to hold an unused microneedle chip may be provided on two side surfaces opposite the opening, and a holder for holding a used microneedle chip may be provided on two side surfaces facing a direction at 90 degrees variance to the aforesaid side surfaces.

The above embodiment has been described in terms of a chip container having two openings and providing four supports to hold the unused microneedle chip at one or another of the openings, and providing a holder that has locking holes for holding a used microneedle chip in the other opening. However, the present invention is not limited to this arrangement inasmuch as a common holder that is capable of holding an unused microneedle chip and a used microneedle chip may be provided at one opening, as in the modification of the chip container shown in FIG. 34. The chip container 320 of the modification shown in FIG. 34 differs from the chip container 120 shown in FIG. 10 in that it is provided with a projection 321d on the edge 321b of the opening 321. An unused microneedle chip 110 and a used microneedle chip 110 can be housed in the single opening 321. The operations of the chip container 320 shown in FIG. 34 when an unused microneedle chip 110 is mounted in the array chuck 340 and when a used microneedle chip 120 is removed from the array chuck 340 are described in detail below with reference to FIGS. 35 and 36. The array chuck 340 is provided with a contact member 342a, which expands a chuck part 342 by abutting the projection 321d of the chip container 320, on one surface of the chuck part 342, as shown in FIGS. 35 and 36.

When mounting an unused microneedle chip 110 in the array chuck 340, the array chuck 340 is inserted into the opening 321 (refer to FIG. 34) of the chip container 320 from a direction in which the projection 321d does not abut the contact 342a, as shown in parts (a) and (b) of FIG. 35. Thus, the microneedle chip 110 can be mounted in the piercing device (array chuck 340) since the chuck part 342 engages the flange 112 of the microneedle chip 110, as shown in parts (c) and (d) of FIG. 35.

When removing an unused microneedle chip 110 from the array chuck 340, the array chuck 340 is inserted into the opening 321 of the chip container 320 from a direction in which the projection 321d abuts the contact member 342a and projection 321d, as shown in parts (a) and (b) of FIG. 36. Thus, the projection 321d abuts the contact member 342a, the chuck part 342 is expanded, and the engagement of the chuck part 342 and the flange 112 of the microneedle chip 110 is released, as shown in part (c) of FIG. 36. Then, the microneedle chip 110 can be removed from the piercing device (array chuck 340), as shown in part (d) of FIG. 36.

What is claimed is:

1. A chip container comprising:
   a first rim that delineates a first opening through which an unused microneedle chip held in the container is removable, the first opening being opened in a direction parallel to an axis of the container;
   a first holder configured to removably hold the unused microneedle chip in the container, the first holder being formed in the first opening so as to allow access through the first opening to the unused microneedle chip held in the container and allow removal of the unused microneedle chip from the container, wherein the first rim is formed with one of a projection and a recess, which is in agreement with the other thereof formed on the microneedle chip;
   a second rim that delineates a second opening through which a used microneedle chip is only insertable for storage in the container and not removal from the container, the second opening being opened in a direction parallel to the axis of the container and opposite to the direction of the first opening; and
   a second holder configured to unremovably hold the used microneedle chip in the container, the second holder being formed in the second opening so as to receive the microneedle chip through the second opening and prohibit removal of the microneedle chip from the container, wherein the second holder comprises at least one beam which is formed with a complementary key structure engageable with a key structure of the microneedle chip, the complementary key structure of the at least one beam and the key structure of the microneedle chip being a key hole and a key projection engageable with each other, and the at least one beam is flexed to lead the key structure of the microneedle chip to engagement with the complementary key structure of the at least one beam and flexed back upon engagement between the complementary key structure and the key structure to secure the engagement.

2. The chip container according to claim 1, wherein the container is tubular in shape having the axis going therethrough, and the first and second openings are opened in the opposite directions coaxial along the axis of the container.

3. The chip container according to claim 1, wherein the first holder comprises a plurality of supports that support the unused microneedle chip in such a manner as to allow removal of the unused microneedle chip through the first opening from the container.

4. The chip container according to claim 1, wherein the plurality of supports support the microneedle chip at intervals to allow access to the microneedle chip through the first opening between adjacent supports.

5. The chip container according to claim 3, wherein the supports each comprise a pillar erected in the first opening for contact with the microneedle chip.

6. The chip container according to claim 1, wherein the second holder comprises at least one release piece provided in the second opening and shaped to at least partially surround, the microneedle chip to prohibit access to the microneedle chip held by the second holder in the container.

7. A chip container kit comprising:
   a microneedle chip comprising microneedles for forming micropores in skin of a living body; and
   a chip container comprising:
     a first rim that delineates a first opening through which the unused microneedle chip held in the container is removable, the first opening being opened in a direction parallel to an axis of the container;
     a first holder configured to removably hold the unused microneedle chip in the container, the first holder being formed in the first opening so as to allow access through the first opening to the unused microneedle chip held in the container and allow removal of the unused microneedle chip from the container, wherein the first rim is formed with one of a projection and a recess, which is in agreement with the other thereof formed on the microneedle chip;
     a second rim that delineates a second opening through which the used microneedle chip is insertable for storage in the container, the second opening being opened in a direction parallel to the axis of the container and opposite to the direction of the first opening; and a second holder configured to unremovably hold the used microneedle chip in the container, the second holder being formed in the second opening so as to receive the microneedle chip through the second opening and prohibit removal of the microneedle chip from the container, wherein the second holder comprises at least one beam which is formed with a complementary key structure engageable with a key structure of the microneedle chip, the complementary key structure of the at least one beam and the key structure of the microneedle chip being a key hole and a key projection engageable with each other, and the at least one beam is flexed to lead the key structure of the microneedle chip to engagement with the complementary key structure of the at least one beam and flexed back upon engagement between the complementary key structure and the key structure to secure the engagement.

* * * * *